United States Patent [19]

Golding

[11] Patent Number: 5,076,728

[45] Date of Patent: Dec. 31, 1991

[54] LANDFILL LINER LEAK DETECTION SYSTEM AND METHOD

[75] Inventor: Randy D. Golding, Tucson, Ariz.

[73] Assignee: Tracer Research Corporation, Tucson, Ariz.

[21] Appl. No.: 514,195

[22] Filed: Apr. 25, 1990

[51] Int. Cl.⁵ .......................... B09B 1/00; E02D 3/00
[52] U.S. Cl. .................................... 405/128; 73/40.7; 405/52
[58] Field of Search ................ 405/128, 129, 52, 270; 73/40.7, 49.2

[56] References Cited

U.S. PATENT DOCUMENTS

| | | | |
|---|---|---|---|
| 4,189,938 | 2/1980 | Heim | 73/40.7 |
| 4,413,503 | 11/1983 | Olivieri | 73/40.7 |
| 4,439,062 | 3/1984 | Kingsbury | 405/129 |
| 4,618,855 | 10/1986 | Harding et al. | 73/40.7 X |
| 4,725,551 | 2/1988 | Thompson | 73/40.7 X |
| 4,748,847 | 6/1988 | Sheahan | 73/40.7 |
| 4,753,551 | 6/1988 | Brueggemann et al. | 405/129 X |
| 4,773,256 | 9/1988 | Saulgeot | 73/40.7 |
| 4,776,208 | 10/1988 | Dimeff | 73/40.7 |
| 4,791,806 | 12/1988 | Wade | 73/40.7 |
| 4,846,604 | 7/1989 | Holtmann | 405/129 X |

FOREIGN PATENT DOCUMENTS 3800504  7/1989  Fed. Rep. of Germany ...... 405/129

Primary Examiner—Dennis L. Taylor
Attorney, Agent, or Firm—David G. Rosenbaum

[57] ABSTRACT

A landfill liner leak detection and monitoring system and method for determining the existence of a leak in the landfill liner. The system consists of a plurality of pipes in the liner underlayer prior to installation of the liner. Each of the plurality of pipes is perforated with pinholes at regular intervals along its length. A tracer chemical is injected into one end of each pipe and air is evacuated through evacuation probed installed in the overlayer. The presence or absence of the tracer in the evacuated sample is indicative of the existence of a leak. The presence of tracer in an evacuated sample will be indicative of the position of the liner leak.

18 Claims, 1 Drawing Sheet

LANDFILL LINER LEAK DETECTION SYSTEM AND METHOD

BACKGROUND OF THE INVENTION

The present invention relates generally to an apparatus and method for testing the integrity of landfill liners principally employed in solid waste disposal sites. More particularly, the present invention discloses an apparatus and method for testing the integrity of liners installed in solid waste landfill sites prior to opening the site for waste disposal. Further, the present invention permits periodic testing of landfill liner integrity after the waste disposal site is open, during the time it is being filled and after the waste disposal site is closed.

In the United States alone about 160 million tons of solid waste are generated each year. This translates to approximately 3½ pounds of refuse per person per day. Landfills currently receive about 80% of all garbage and are rapidly filling up. (See, e.g., 107 *U.S. News & World Report*, No. 25, pp. 60–61 (Dec. 25, 1989)). The rapid growth of governmental legislation pertaining to management of waste disposal, coupled with the growing public concern about the long and short-term environmental impact of waste disposal facilities, has increased design complexity of waste disposal facilities. Moreover, the rapidly declining availability of landfill solid waste disposal sites is reaching a critical point. New landfill sites will have to be opened, or other less environmentally safe methods of solid waste disposal, e.g., ocean dumping, incineration, etc., will have to be employed. The public's awareness of the waste disposal dilemma has only recently captured broad public attention. With this attention, the public has been and will, increasingly, demand more and safer disposal sites.

Most landfills have an impermeable liner which acts as a leakage barrier between the landfill and the underlying soil. When building a new landfill site, it is customary to prepare an underlayer of compacted sand or clay which serves as a bed for the liner. After installation of the liner, another sand or clay overlayer is provided on top of the liner. The disposed trash is then filled onto the composite layers. The proper function of waste disposal facilities depends upon the integrity of the landfill liner. Generally, liner failure is not detected until the waste leaches into the underlying soil and causes environmental damage.

Under present efforts to prevent leachate from reaching the subsurface soil area underneath the landfill, numerous systems have been developed to test liner integrity:

a) leak prevention through an induced hydraulic gradient between a plurality of liners (See, Mutch, R. D., U.S. Pat. No. 4,335,978, Issued June 22, 1982, *Induced Intragradient System for Secure Landfill*);

b) collecting leachate and detecting the presence of leachate in a sump (See, Turner, D. M., U.S. Pat. No. 4,810,131, Issued Mar. 7, 1989, *Landfill Leachate Collection and Leak Detection Sump System*);

c) providing a liquid collection zone at a level beneath the landfill and determining the presence of leachate in the liquid collection zone (See, Bennett, R. J., U.S. Pat. No. 3,505,820, Issued Apr. 14, 1970, *Leak Detection for Lined Reservoirs*);

d) collecting and treating landfill leachate (See, Lavingne, R. L., et al, U.S. Pat. No. 4,276,164, Issued June 30, 1981, *Effluent Treatment System: Leachate, Landfill*);

e) detecting loss of gas pressure in a gas pressurized annulus about an underground storage zone (See, Butler, W. J., U.S. Pat. No. 4,474,053, Issued Oct. 10, 1984, *Storage or Disposal Cavern Leak Detection and Loss Prevention*);

f) applying an external electrically conductive metal foil liner to the impermeable landfill liner, applying an electrical potential to the liner to determine if a leak exists (See, Benard, G. J., et al, U.S. Pat. No. 3,252,155, Issued May 17, 1966, *Liquid Receptacle and Method for Preparing Same*);

g) providing a tank liner with fluid passageways to conduct fluid entering a tank to a drain pipe; (See, Wagner, R., U.S. Pat. No. 4,787,772, Issued Nov. 29, 1988, *Device for Detecting Leaks in Underground Fluid Tanks*);

h) using a leak flow rate measuring apparatus, to determine the rate of flow of an impounded liquid through an opening in a geomembrane liner, which employs a pair of spaced voltage measuring sensors which measure voltage across a liquid passage (See, Cooper, John, W., U.S. Pat. No. 4,755,757, Issued July 5, 1988, *Fluid Leak Detection System for Determining the Fate of Leakage Through a Geomembrane*);

i) disposing an electrically conductive liquid between two contiguous liners, applying an electrical current to the liquid and sweeping the landfill surface with magnetic surfaces for magnetic field variations indicating leakage of the fluid through the lower liner (See, Converse, M. E., et al, U.S. Pat. No. 4,740,757, Issued Apr. 26, 1988, *Method and Apparatus for Locating Leaks in a multiple layer Geomembrane Liner*);

j) using an electronic directional potential analyzer having a differential voltage detection probe which is moved through a conducting liquid contained within a liner to measure a differential potential between electrodes on the probe relative to positions in the liner (See, Converse, M. E., et al, U.S. Pat. No. 4,725,785, Issued Feb. 2, 1988, *Directional Potential Analyzer Method and Apparatus for Detecting and Locating Leaks in Geomembrane Liners*);

k) employing a liner having a sheet of electrically insulating material supported by an electrically conductive medium, applying an electrical potential between fluid retained within said liner and the supporting medium and determining whether there is a change in the electrical potential as an electrode is moved about the fluid surface (See, Boryta, D. A., et al, U.S. Pat. No. 4,543,525, Issued Sept. 24, 1985, *Method for Determining a Leak in a Pond Liner of Electrically Insulating Sheet Material*); or l) providing a set of channels adjacent to a liner, each of the channels having a plurality of lateral openings into a surrounding casing and a series of connecting tubes connected to the channels to locate leaks in nuclear reactor liners (see, Escherich, K. H., et al, U.S. Pat. No. 4,341,110, Issued Mar. 23, 1982, *System for Locating Leaks in the Liner of a Pressure Vessel Equipped with Cooling Tubes; for Nuclear Reactors*).

There is a recognized need, therefore, for an apparatus and method for testing the integrity of landfill liners prior to opening of the landfill for refuse disposal and for periodically testing the integrity of landfill liners.

SUMMARY OF THE INVENTION

It is, therefore, a principal object of the invention to provide a landfill liner leak detection system and method for determining the existence of a leak in the landfill liner. This objective is accomplished by providing a plurality of pipes in the liner underlayer prior to installation of the liner. Each of the plurality of pipes is perforated with pinholes at regular intervals along its length. A tracer chemical is injected into one end of each pipe and air is evacuated through evacuation probed installed in the overlayer. The presence or absence of the tracer in the evacuated sample is indicative of the existence of a leak. The presence of tracer in an evacuated sample will be indicative of the position of the liner leak. After liner integrity is confirmed, the landfill may be opened, periodic monitoring of liner integrity is accomplished by reversing the testing process; a unique tracer is injected into the refuse layer or into the overlayer and air samples are evacuated from the pipes underneath the liner. Again, the presence or absence of the tracer in the evacuated gas samples is determinative of the existence of a leak in the landfill liner. The approximate location of the liner leak may be determined by serially probing the overlayer and either evacuating samples or injecting tracer along the lengthwise axis of the underlying pipe.

Selection of the appropriate tracer may be made in accordance with the disclosures in U.S. Pat. Nos. 4,709,577 and 4,725,551 or with reference to co-pending applications Ser. Nos. 07/303,459 and 07/378,415, which are hereby incorporated by reference thereto.

These and other features, objects and advantages of the present invention will become more apparent to those skilled in the art from the following more detailed description of the invention, with reference to the preferred embodiments thereof, taken with the accompanying drawings, in which like features are identified by like reference numerals.

DETAILED DESCRIPTION OF THE PREFERRED EMBODIMENTS

Figure 1:
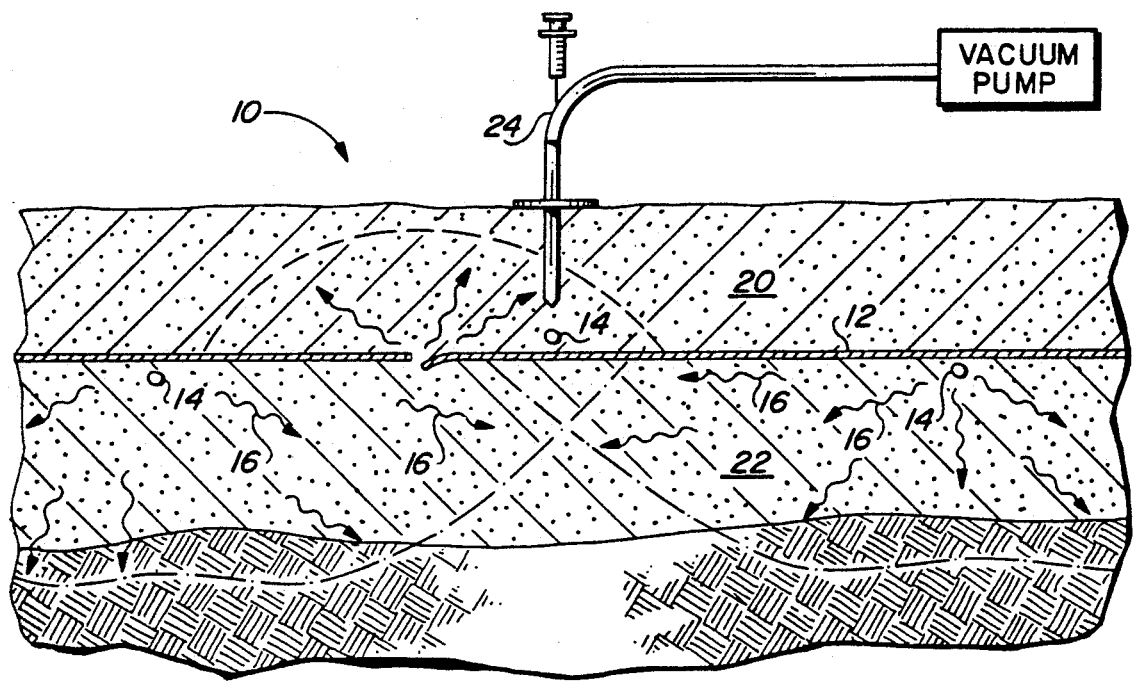
FIG. 1 is a diagrammatic side elevational view of the landfill liner leak detection system in accordance with the preferred embodiment of the present invention.

With reference to the accompanying Figures, there is shown a landfill liner leak detection and monitoring system 10 in accordance with the preferred embodiment of the present invention. System 10 consists of a liner member 12, which is made of any suitable chemically and environmentally inert material, such as is known in the art. A plurality of hollow tubular members 14 are provided in the sandy underlayer 22. The plurality of hollow tubular members 14 may be made of an inert material such as polyethylene. In accordance with the present invention, each of the tubular members 14 are open at a first end and closable at a second end. The open first end of each tubular member 14 is accessible from the perimeter of the landfill site. Optionally, the open first end of each of the tubular members 14 may be manifolded together to a common source of volatile tracer. The closable second end of each tubular member 14 is also preferably accessible from the perimeter of the landfill site and may, optionally, be looped back to the same point as or in close proximity to the open first end of each tubular member 14. In this manner, both ends of the tubular members 14 are readily accessed for tracer injection and/or air withdrawal.

Figure 2:
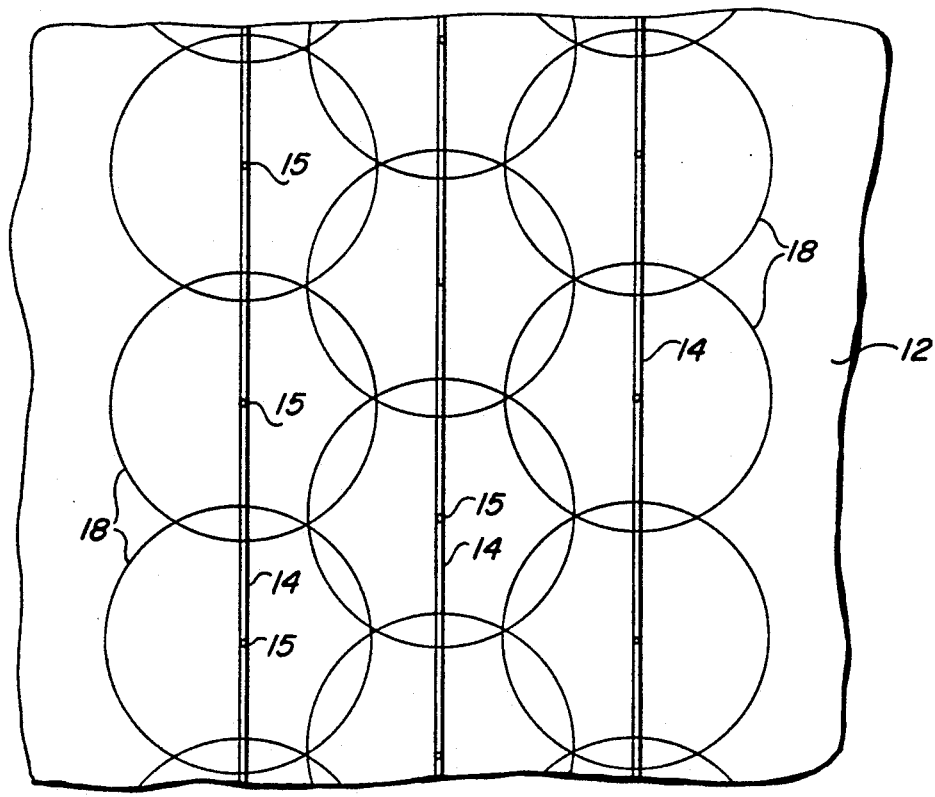
FIG. 2 is a top elevational view of the landfill liner leak detection system in accordance with the preferred embodiment of the present invention.

Each of the plurality of hollow tubular members 14, may be provided immediately underneath the liner member 12 and in close proximity thereto, may be attached to the bottom surface of the liner member 12, or may be molded as channels in association with the liner member 12. As illustrated with reference to FIG. 2, the plurality of hollow tubular members 14 are distributed in a parallel array and have at least one perforation 15 in the wall of the hollow tubular member 14.

The plurality of hollow tubular members 14 have at least one of a plurality of openings which permit a volatile tracer to be emitted from the tubular member 14. Where more than one opening is used, as will occur in typical large scale landfill sites, the perforations are preferably located along a lengthwise aspect of each of the plurality of hollow tubular members 14. In accordance with an alternate preferred embodiment of the invention, the tubular members 14 may be made of a compressed granulated rubber material, such as soil irrigation tubing, in which the interstitial spaces between the rubber granules serve as the openings to emit the tracer from the tubular member 14. Regardless of the material selected for the tubular members 14, tubular members 14 should exhibit sufficiently low wall permeability such that, under ambient pressure, the tubular members are substantially impermeable to fluid, such as subsurface water. For example, where the compressed granulated rubber material is employed, it has been found that permeability is within the range of about 0.3 to about 10 cubic feet per minute over a five hundred foot length of tubing pressurized to 100 p.s.i.. Those skilled in the art will understand and appreciate that this low wall permeability will be sufficient to permit gas permeation, while substantially eliminating fluid permeability at ambient pressure.

Where the material of the tubular members 14 is substantially uniform, i.e., has no interstitial openings, at least one of a plurality of perforations 15 must be made in the wall of tubular members 14. According to the preferred embodiment of the present invention, the size and number of the perforations 15 are selected to ensure that the volatile tracer escapes from the tubular members 14 along its entire length. The number of perforations 15 are selected according to the length of the hollow tubular members 14 needed to completely underlay the liner member 12. The linear spacing of the perforations 15 is selected according to the soil dispersion characteristics of the tracer 16 selected for use in testing liner integrity.

As described in U.S. Pat. Nos. 4,725,551 and 4,709,557, the tracer employed is preferably a highly detectable volatile organic tracer such as a fluorinated halocarbon compound, having a boiling point within the range of about $-72°$ to about $150°$ C. The tracer is preferably selected from the group consisting of fluorinated halocarbons, methanes, and ethanes having a boiling point in the liquid phase in the range of about $-72°$ C. and $150°$ C. More specifically, the tracer may consist of halogenated methanes, halogenated ethanes, halogenated ethenes, halogenated alkanes, halogenated alkenes, sulfurhexafluoride, perfluorodeoalin, and perfluoro 1,3 dimethyloyclohexane. The group of halogenated methane is preferably selected from the group consisting of chlorobromodifluoromethane, trichlorofluoromethane, trifluoroiodomethane, trifluorobromomethane, dibromodifluoromethane, dichlorodifluoromethane and tetrafluoromethane. The halogenated ethane is preferably selected from the group consisting of dichlorotetrafluoroethane, hexafluoroethane, trichlorotrifluoroethane, dibromotetrafluoroethane and tetrachlorodifluoroethane. The halogenated ethene is preferably tetrafluoroethene. The particular tracer employed will be selected on site and must be distinct from any chemical background in the soil area. These tracer chemicals are easily detected at extremely low concentrations, i.e. in the parts per trillion range, by gas chromatography. By introducing these tracer chemicals at very low concentrations (e.g., parts per million), defects in the liner can be detected without introducing large quantities of foreign chemicals into the environment.

An important aspect of the present invention is that the linear spacing of perforations 15 in each of the plurality of hollow tubular members 12, when coupled with selected lateral spacing of each of the plurality of hollow tubular members 12, provides for the development of overlapping regions of tracer influence 18 in the sandy underlayer 22. Establishing the overlapping regions 18 serves to form a tracer layer in the sandy underlayer 22 and ensures that virtually the entire surface area of the liner member 12 is exposed to this tracer layer. If a defect exists in the landfill liner, the tracer will escape through the defect and may be detected in air samples withdrawn from the sandy overlayer 20. Once the presence of the defect is determined, only that portion of the sandy overlayer is removed and the defect exposed for repair.

In operation, after the landfill excavation is complete, the landfill liner leak detection and monitoring system 10 of the present invention is installed and the sandy overlay 20 placed thereupon. A mixture of tracer in air will be pumped into each of the plurality of hollow members 14 until each member 14 is filled with the tracer/air mixture. The tracer/air mixture will continuously be injected until the overlapping regions of tracer influence 18 are established. A sampling probe 24, connected to a vacuum pump (not shown), is inserted into the sandy overlayer 20 and air samples may be collected and analyzed for the presence of tracer in the sample. Where tracer is detected, a leak in the liner member 12 exists. Once the liner member 12 has been found to be leak-free, the land-fill may be certified and opened.

In accordance with the present invention, system 10 also facilitates routine or periodic monitoring of the integrity of liner member 12 after the landfill is accepting garbage. By withdrawing air samples from each of the plurality of hollow tubular members 14, the presence foreign chemicals in air samples withdrawn from the sandy underlayer 22 will indicate the existence of a leak in the landfill liner member 12. Moreover, any changes in the concentration of the foreign chemical, over time, in the withdrawn air samples will provide valuable information concerning the volume and rate of the leak. To facilitate such routine or periodic monitoring of the liner member 12, it is desirable to provide another array of tubular members 13 in the overlayer. As illustrated diagrammatically in FIG. 1, the tubular members 13 may be positioned in the overlayer parallel to and between the tubular members 14. The tubular members 13 in the overlayer may be used to withdraw gas samples to determine the existence of a leak, evidenced by the presence of tracer emitted from the tubular members 14 in the underlayer. Alternatively, the tubular members 13 may be used to inject tracer above the liner and establish regions of tracer influence in the overlayer, whereby gas samples are withdrawn from the tubular members 14 in the underlayer. In this manner, at least one set of tubular members 13 or 14 will always be available for tracer injection or gas sampling while the landfill is in service or thereafter.

Thus, it will be appreciated by those skilled in the art, that a new and useful system and method for detecting leaks in landfill liners has been described and disclosed. While there has been described what, at present, is considered to be the preferred embodiments of the present invention, it will be appreciated that various modifications and alterations may be made therein without departing from the true scope and spirit of the present invention, which the claims appended hereto are intended to cover.

I claim:

1. A system for detecting the existence of a leak in a landfill liner, where the landfill liner is interposed between an underlayer and an overlayer of earthen material, wherein the system comprises:
    a plurality of gas permeable hollow tubular members horizontally disposed in the earthen underlayer in close proximity to the landfill liner and provided in a parallel array underneath the landfill liner, each of said plurality of hollow tubular members having a first closable end and a second open end;
    volatile tracer means for providing a detectable component in a gas sample, said volatile tracer means being mixed with air in each of said plurality of hollow tubular members; and
    sampling means for withdrawing gas samples from the earthen overlayer.

2. The system according to claim 1, wherein said system further comprises at least one air injection means for injecting an air/tracer means mixture, under pressure, into each of said plurality of hollow tubular members.

3. The system according to claim 1, wherein said plurality of hollow tubular members are affixed to the landfill liner.

4. The system according to claim 1, wherein said plurality of hollow tubular members further comprise channels integral with the landfill liner.

5. The system according to claim 1, wherein each of said plurality of hollow tubular members further comprise a plurality of linearly spaced apertures along a lengthwise aspect of said hollow tubular member.

6. The system according to claim 5, wherein said plurality of hollow tubular members are positioned such that said tracer means injected into each of said plurality of hollow tubular members and escaping through walls of said hollow tubular members forms overlapping regions of tracer means influence in the earthen underlayer.

7. The system according to claim 1, wherein said tracer means is selected from the group consisting of halogenated halocarbons, methanes, ethanes, alkanes, ethenes and alkenes.

8. The system according to claim 1, wherein said tracer means is a fluorinated halocarbon compound.

9. The system according to claim 1, wherein said tracer means is selected from the group consisting of halogenated methanes, halogenated ethanes, sulfurhexafluoride, perfluorodecalin, and perfluoro 1,3 dimethylcyclohexane.

10. The system according to claim 1, wherein said tracer means has a boiling point in the range of about $-72°$ C. and $150°$ C.

11. The system according to claim 1, wherein said tracer means is a halogenated methane selected from the group consisting of chlorobromodifluoromethane, trifluoroiodomethane, trifluorobromomethane, dibromodifluoromethane, dichlorodifluoromethane and tetrafluoromethane.

12. The system according to claim 1, wherein said tracer means is a halogenated ethane selected from the group consisting of dichlorotetrafluoroethane, hexafluoroethane, trichlorotrifluoroethane, dibromotetrafluoroethane and tetrachlorodifluoroethane.

13. The system according to claim 1, wherein said tracer is a halogenated ethene comprising tetrafluoroethene.

14. A method for detecting leaks in a landfill liner of the type having an overlayer and an underlayer, comprising the steps of:
    horizontally disposing a plurality of hollow tubular members in a parallel array in the underlayer, each of said plurality of hollow tubular members having a first closable end, a second open end and having gas permeable walls thereof;
    disposing the landfill liner over the plurality of tubular members;
    providing volatile tracer means for providing a detectable component in a gas sample;
    injecting said volatile tracer means into each of said plurality of hollow tubular members under pressure and exerting a positive pressure within each of said plurality of hollow tubular members, thereby causing said volatile tracer means to pass through the gas permeable walls of the plurality of hollow tubular members and into the underlayer underneath the landfill liner;
    withdrawing gas samples from the overlayer above the landfill liner; and
    analyzing said withdrawn gas samples to determine the presence of said volatile tracer means, thereby indicating the presence of a leak in the landfill liner.

15. The method according to claim 14, wherein said step of injecting an air/tracer means mixture further comprises the step of injecting said air/tracer means mixture until said tracer means escapes through the gas permeable walls and forms overlapping regions of tracer means influence in the underlayer.

16. A system for detecting the existence of a leak in a landfill, comprising:
    an excavated landfill basin having an underlayer for the landfill provided in the landfill basin;
    a plurality of hollow tubular members horizontally disposed on at least one of one or in the underlayer in a parallel array, each of said plurality of hollow tubular members having a first closable end, a second open end and having walls thereof which are capable of transmitting a gas therethrough, but are substantially resistant to the passage of liquid therethrough at ambient pressure;
    a landfill liner disposed above said plurality of hollow tubular members;
    an overlayer of a backfilled material disposed on top of said landfill liner;
    volatile tracer means for providing a detectable component in a gas sample;
    means for injecting said volatile tracer means, under pressure, into each of said plurality of hollow tubular members; and
    sampling means for withdrawing gas samples from the overlayer.

17. The system according to claim 16, wherein each of said plurality of hollow tubular members further comprise a plurality of linearly spaced apertures along a lengthwise aspect of said hollow tubular member.

18. The system according to 16, further comprising overlapping regions of tracer means influence in the underlayer.

* * * * *

UNITED STATES PATENT AND TRADEMARK OFFICE
CERTIFICATE OF CORRECTION

PATENT NO. : 5,076,728
DATED : December 31, 1991
INVENTOR(S) : Randy D. Golding

It is certified that error appears in the above—identified patent and that said Letters Patent is hereby corrected as shown below:

Column 6:

In claim 1, line 2, change "interposed" to --interdisposed--.

Column 8:

In claim 16, line 6, after "of", delete "one" and insert --on--.

Signed and Sealed this

Fifteenth Day of June, 1993

Attest:

MICHAEL K. KIRK

Attesting Officer

Acting Commissioner of Patents and Trademarks